(12) United States Patent
Weksler et al.

(10) Patent No.: US 9,261,713 B1
(45) Date of Patent: Feb. 16, 2016

(54) ELECTRONICALLY TRANSITIONING LENSES

(71) Applicant: Lenovo (Singapore) Pte. Ltd., Singapore (SG)

(72) Inventors: Arnold S. Weksler, Raleigh, NC (US); Russell Speight VanBlon, Raleigh, NC (US); Nathan J. Peterson, Durham, NC (US); John Carl Mese, Cary, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 14/502,481

(22) Filed: Sep. 30, 2014

(51) Int. Cl.
*G02C 7/10* (2006.01)
*G02C 11/00* (2006.01)
*A61B 3/113* (2006.01)
*A61B 3/11* (2006.01)
*A61B 3/00* (2006.01)

(52) U.S. Cl.
CPC .............. *G02C 7/101* (2013.01); *A61B 3/0025* (2013.01); *A61B 3/112* (2013.01); *A61B 3/113* (2013.01); *G02C 11/10* (2013.01)

(58) Field of Classification Search
CPC ...... A61B 3/0008; A61B 3/112; A61B 3/113; G02C 7/10; G02C 7/101
USPC ........ 351/204, 209, 210, 221, 246, 44, 159.6, 351/159.65
See application file for complete search history.

(56) References Cited

U.S. PATENT DOCUMENTS

| 2011/0080421 A1* | 4/2011 | Capener | G09G 5/10 345/589 |
| 2014/0055747 A1* | 2/2014 | Nistico | A61B 3/113 351/206 |

* cited by examiner

*Primary Examiner* — Huy K Mai
(74) *Attorney, Agent, or Firm* — Ference & Associates LLC

(57) ABSTRACT

One embodiment provides a method, comprising: capturing, using a sensor, data with an ambient brightness; comparing, using a processor, the data with a rule set; determining, using a processor, an amount of tinting of glasses needs adjusted based upon the comparison of the data to the rule set; and adjusting, using a processor, the amount of tinting of glasses. Other aspects are described and claimed.

25 Claims, 3 Drawing Sheets

ELECTRONICALLY TRANSITIONING LENSES

BACKGROUND

Many people wear glasses to correct a variety of optical issues (e.g., near-sightedness, far-sightedness, astigmatism, etc.). Wearers of glasses tend to have few options when selecting a type of sunglass. Some choose to buy prescription sunglasses, clip-on sunglasses, or may choose to wear standard sunglasses rather than their prescription glasses. Others may choose to wear photochromatic glasses such as transitional lenses. These may allow a person to wear a single pair of glasses in both light and dark places, without the need to switch to sunglasses. The typical transitional lens works through a chemical reaction to ultraviolet (UV) radiation. In some cases, transitional lenses may work when exposed to visible light, which may work when a person is in a location where UV light may be blocked such as a vehicle.

BRIEF SUMMARY

In summary, one aspect provides a method, comprising: capturing, using a sensor, data with an ambient brightness; comparing, using a processor, the data with a rule set; determining, using a processor, an amount of tinting of glasses needs adjusted based upon the comparison of the data to the rule set; and adjusting, using a processor, the amount of tinting of glasses.

Another aspect provides an information handling device, comprising: a sensor; a processor operatively coupled to the sensor; a memory device that stores instructions executable by the processor to: capture, using the sensor, data associated an ambient; compare the data with a rule set; determine an amount of tinting of glasses needs adjusted based upon the comparison of the data to the rule set; and adjust the amount of tinting of glasses.

Another aspect provides an information handling device, comprising: a sensor; a processor operatively coupled to the sensor; a memory device that stores instructions executable by the processor to: capture, using the sensor, data associated with an ambient brightness; receive a signal indicating tinting of glasses needs adjusted based upon the captured data; and adjust an amount of tinting of glasses.

A further aspect provides an information handling device, comprising: a processor; a memory device that stores instructions executable by the processor to: receive data, captured by a sensor, associated with an ambient brightness; compare the data with a rule set; and determine an amount of tinting of glasses needs adjusted based upon the comparison of the data to the rule set.

A further aspect provides a product, comprising: a storage device having code stored therewith, the code being executable by a processor and comprising: code that captures, via a sensor, data associated with a wearer's eye; code that identifies, using a processor, at least one characteristic associated with an ambient brightness based on the captured data; code that compares, using a processor, the at least one characteristic with a rule set; code that determines, using a processor, an amount of tinting of glasses needs adjusted based upon the comparison of the at least one characteristic to the rule set; and code that adjusts, using a processor, the amount of tinting of glasses.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
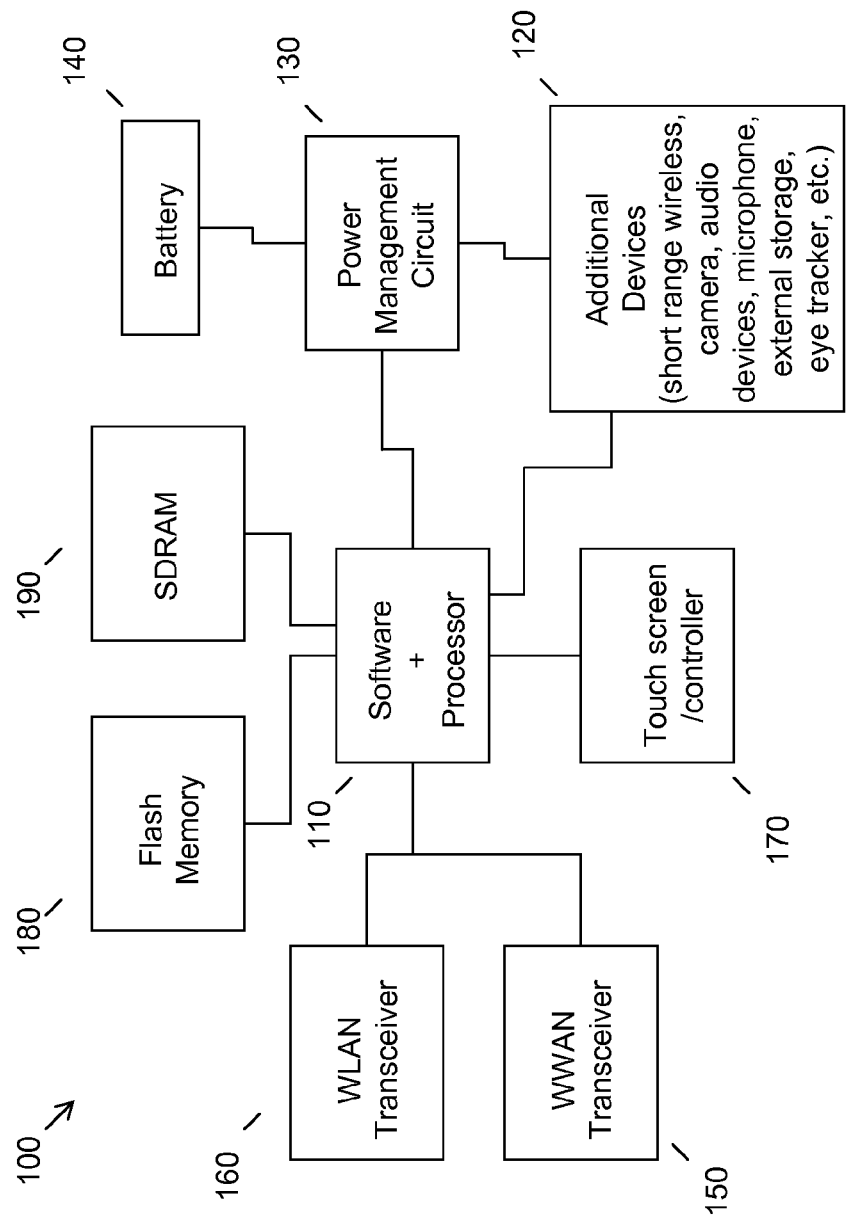
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Many people wear glasses to correct a variety of optical issues (e.g., near-sightedness, far-sightedness, astigmatism, etc.). When these wearers of glasses move to a location with an increased amount of light (e.g., outside, in a car, etc.), the options for sunglasses may be limited. Those wearers of glasses who may have a weaker prescription may choose to wear standard sunglasses rather than wearing their glasses. For obvious reasons this may not be very safe. Another option is to purchase prescription sunglasses. However, these may be very costly. Additionally, the wearer must have some place to put the glasses or sunglasses while they are not being worn. A cheaper alternative may be to buy a pair of glasses which additionally has some type of clip-on sunglasses. However, this may limit the type or style of glasses that a wearer can choose from.

One solution is transitional lenses. Generally, transitional lenses work through a chemical reaction to UV light. Due to this, in some instances the lenses may not darken. For example, when in a car, the windshield may block UV light, thereby decreasing the effectiveness of the transitional lens. Some transitional lenses react to visible light, which allows them to darken even in places such as a car where the windshield blocks the UV light. However, the activation by visible light is generally not as great as that caused by UV light, which means that the glasses may not get as dark.

Additionally, transitional lenses may not get as dark as a wearer may like. The darkness of the transitional lens is dependant on the amount of coating and the amount of UV or visible light. Another disadvantage to a traditional transitional lens is the rate at which the lenses change from clear to dark and from dark to clear. This can be a slow process where, when a wearer steps into a light place from a dark place, the wearer may have to wait a few seconds while the lenses change. The transition from a dark place to a light place may also take a few seconds.

In addition, when a wearer is in a location where the glasses have darkened to account for the increase in UV or visible light, the glasses may be too dark for the wearer to see particular objects. For example, if a wearer is inside an automobile and looking at the road, the transitional lenses may be the correct darkness. However, if the wearer looks at something in the car, for example a navigation system, cellular phone, instrument panel, and the like, the transitional lenses may be too dark to clearly see the object.

Accordingly, an embodiment provides a method of electronically transitioning lenses which may allow for a quicker transition of the lenses from dark to light and vice versa. In addition an embodiment may allow for wearer configurability which may allow a wearer to adjust how dark or light the lenses may get when exposed to different variations in light. One embodiment may additionally transition between dark and light depending on where the wearer is looking. This may, for example, allow a wearer to look at the road and the glasses are appropriately adjusted for that brightness. A wearer may then look at something within the car and the glasses may adjust to be appropriately adjusted for looking at the object within the car.

An embodiment may capture data associated with an ambient brightness. This data may include data associated with the wearer's pupil. Alternatively or additionally, this data may include gaze tracking data, which may be used to determine where the wearer is looking Other data may be captured, for example, the UV light content, visible light content, or other data which may be associated with an ambient brightness. One example embodiment may identify the size of the wearer's pupil. This information may allow an embodiment to determine whether the location where the wearer is currently located is too bright for the wearer. Another example characteristic may be the level of ambient brightness associated with where the wearer is looking An embodiment may then compare this data with a rule set. This rule set may include information regarding data associated with an ambient brightness. The rule set may additionally include information regarding an amount of tinting. For example, the rule set may include a desired pupil size and an amount of tinting required to reach that desired pupil size. As another example, the rule set may include a level of ambient brightness and the amount of tinting desired at this level of ambient brightness. In one embodiment, the data included in the rule set may be configured by the wearer.

Based upon the comparison, an embodiment may determine that the amount of tinting of the wearer's glasses needs adjusted. For example, an embodiment may determine that the wearer's pupil size is too large and the amount of tinting needs to be increased. An embodiment may then adjust the tinting of the glasses to reach the desired tinting level. This level of tinting may be adjusted by the wearer. For example, if the wearer prefers darker sunglasses, the wearer may be able to increase the amount of tinting.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally devices 120 are commonly included, e.g., an image sensor such as a camera, an eye tracker, optical sensor, etc. System 100 often includes a touch screen 170 for data input and display/rendering. System 100 also typically includes various memory devices, for example flash memory 180 and SDRAM 190.

Figure 2:
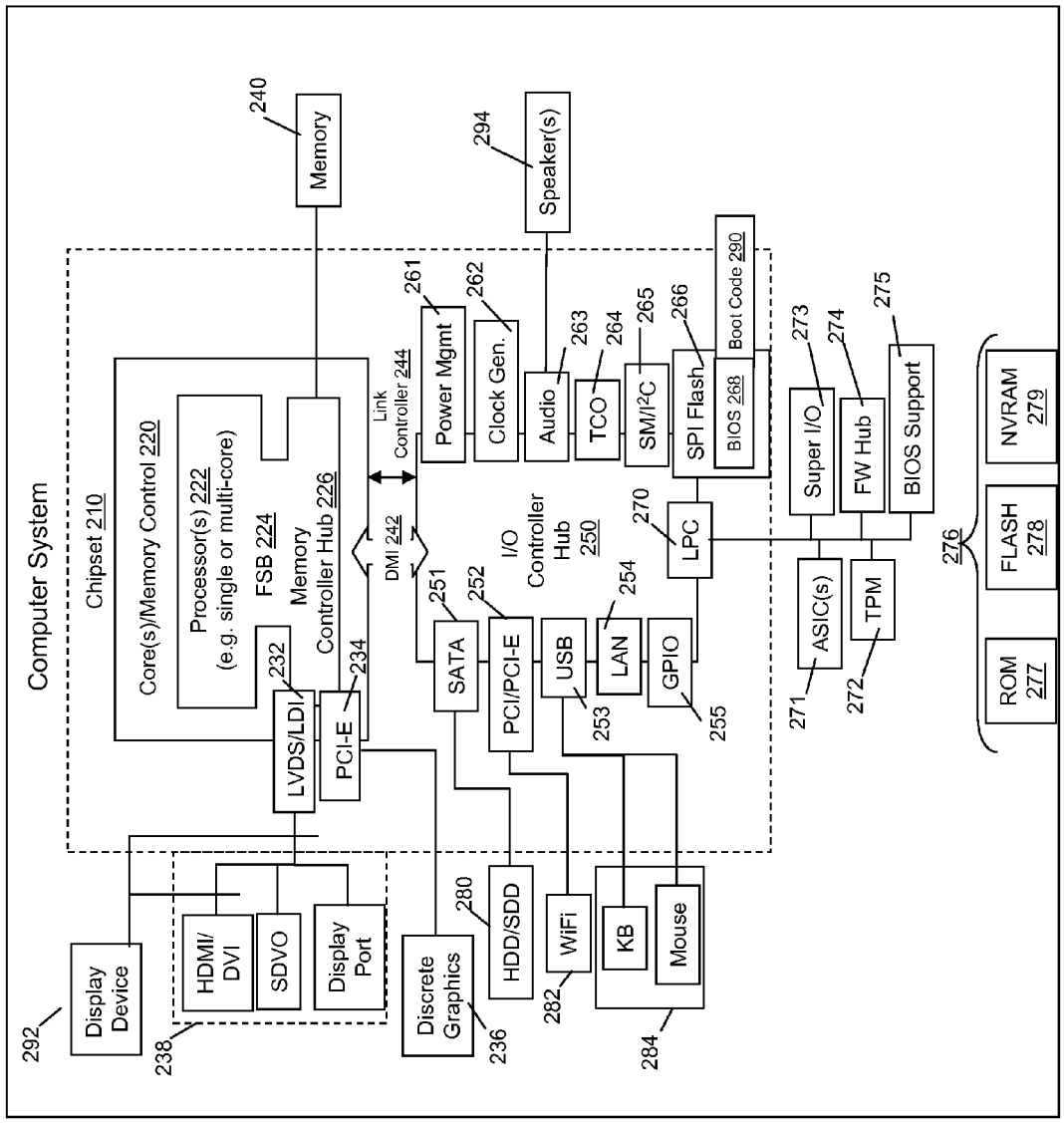
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a LVDS interface 232 for a display device 292. A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, eye tracker, optical sensor, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices which may include glasses including electronically transitioning lenses. For example, the glasses may comprise an optical glass with a material that allows or supports an electrical connection or electrical pathways. For example, these glasses may comprise or include an LCD, LED display, support a backlight, support a heads-up display, and the like. The glasses may additionally include information handling device circuitry including a processing device, which may be fully integrated into the frames or lenses.

Alternatively or additionally, information handling device circuitry, as for example outlined in FIG. 1 or FIG. 2 may be connected to the glasses. For example, the glasses may not include a processing unit, rather the data captured by the sensor on the glasses is sent to an information handling device, for example, a smart phone, tablet, independent information handling device built for the glasses, or the like. This information handling device may communicate with the glasses through a wired or wireless connection. For example, the glasses may be operatively connected to and communicate with the information handling device through Bluetooth, a wireless network, a type of short range communication protocol, and the like.

Figure 3:
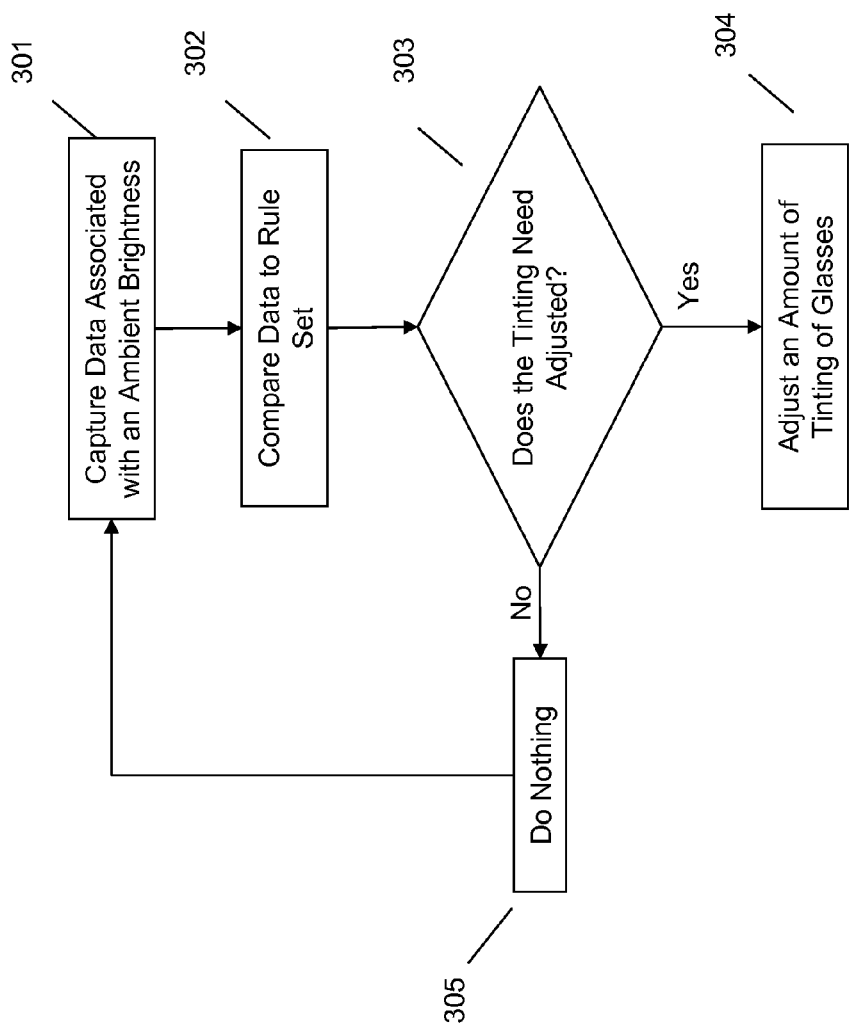
FIG. 3 illustrates an example method of electronically transitioning lenses.

Referring now to FIG. 3, an embodiment may capture data associated with an ambient brightness at 301. This capturing may be accomplished using a sensor, for example, a camera that captures visual images, an image capture device that captures non-visible light, an eye tracker, an optical sensor, and the like. This sensor may be mounted on the glasses or may alternatively be integrated into the lens or glass frame. The data captured may include data such as the information relating to the wearer's pupil, for example, the size of the wearer's pupil. Alternatively or additionally, the data may include gaze tracking data, for example, the location where the wearer is looking, the level of ambient brightness at that location, and the like. The data captured is intended to assist in determining whether tinting of the glasses is necessary. Therefore, other data may be captured to assist in this determination. For example, the glasses may include a sensor that detects, captures, and/or determines, for example, ambient brightness, UV light levels, visible light levels, contrast between two locations, and the like, regardless of any information regarding the wearer's eye.

In one example embodiment, the glasses may capture data associated with the wearer's pupil. It may then identify the size of the wearer's pupil as an indication of ambient brightness. For example, when a wearer walks into a building an embodiment may use an image capture device to identify that the wearer's pupil size is increasing. An embodiment may then identify that the ambient brightness is of a lower value than where the wearer was previously located.

In another example embodiment, the glasses may capture gaze tracking data. It may then, using the gaze tracking data, identify the location associated with the wearer's gaze and determine the ambient brightness at the location associated with the wearer's gaze. In other words, an embodiment may determine where the wearer is looking and once that location has been determined an embodiment may determine how bright that location is. For example, if a wearer is driving a car the ambient brightness within the car may be equal to one value, but the brightness outside the vehicle may be a different value. If an embodiment determines that the wearer is looking at the road, an embodiment may use the ambient brightness outside the vehicle to make the identification. On the other hand, if an embodiment identifies that the wearer is looking at an object within the car, an embodiment may use the ambient brightness inside the car to make the identification.

At 302, an embodiment may compare the data to a rule set. The rule set may comprise data including the data and an associated amount of tinting. For example, the rule set may indicate that for a particular characteristic the amount of tinting should be a particular value. In one example embodiment, the rule set may comprise a level of ambient brightness and an amount of tinting at that level of brightness. In other words, the rule set may include an amount of tinting that is desired when the ambient brightness is a particular value. For example, the rule set may indicate that if the ambient brightness is a particular luminosity, the amount of tinting should be a particular value.

In an additional example embodiment, the rule set may comprise data including a pupil size and an amount of tinting based upon the pupil size. In other words, the rule set may include data indicating the amount of tinting desired when the pupil is a particular size. For example, if a wearer is walking outside a building, the wearer's pupil size may decrease. The rule set may indicate that for this decreased pupil size, the amount of tinting should be a particular value. In one embodiment, the data within the rule set may be configured by the wearer. For example, the wearer may modify the rule set to a particular amount of tinting when the pupil is a particular size or when the ambient brightness is a particular value. For example, a wearer may want the glasses to be darker when they are outside. The wearer may then be able to adjust the amount of tinting used within the rule set based upon their preference.

Within one embodiment, the rule set may comprise data including an ambient brightness profile. This ambient brightness profile may include a variety of information such as information regarding the type of lighting that an embodiment is detecting. For example, an embodiment may adjust the tinting differently if the wearer is in a location with fluorescent lighting as opposed to a location with incandescent lighting. One embodiment may capture additional information and may create an ambient brightness profile based upon this additional information. For example, an embodiment may detect that a wearer is driving a car and may adjust the tinting in accordance with the ambient brightness profile associated with being a driver of a vehicle. As an alternative example, an embodiment may determine that the wearer is the passenger in a vehicle and may adjust the tinting in accordance with an ambient brightness profile associated with being a passenger. Other information may be included in or have an on effect the ambient brightness profile. For example, the ambient brightness profile may include information regarding indoors versus outdoors, individual positioning, motion detection, and the like.

In one embodiment, the ambient brightness profile may include default values and/or profiles. Additionally or alternatively, the ambient brightness profile may be wearer configurable. For example, a wearer may prefer that the glasses are darker in natural lighting than if the wearer is located in a location with incandescent lights. One embodiment may allow the wearer to connect the glasses or the processor of the glasses to an information handling device to adjust or add any wearer configurable data including, for example, an ambient brightness profile, amount of tinting (discussed below), information within a rule set, and the like.

Based upon the comparison at 302, an embodiment may make the determination of whether the tinting of the glasses needs adjusted at 303. This determination may be made by comparing the amount of tinting found in the rule set to the amount of tinting the glasses currently have. For example, an embodiment may determine that based upon the wearer's pupil size, the amount of tinting should be 50%. The current amount of tinting of the glasses is 25%. Based upon the comparison, an embodiment may determine that the tinting level should be adjusted. As another example, if a wearer is outside looking at the horizon, the glasses may be adjusted to the correct tinting level for that application. If, however, the wearer looks down at their cell phone, an embodiment may determine, based upon the level of ambient brightness at the phone, that the tinting should be adjusted because the amount of tinting does not match the amount of tinting needed for the level of ambient brightness at the cell phone.

If an embodiment determines that the tinting does not need adjusted at 303, it may do nothing at 305 and continue to capture data at 301. If, however, an embodiment determines that the tinting does need adjusted at 303, an embodiment may adjust the amount of tinting of the wearer's glasses at 304. The amount of tinting may be measured in a variety of ways. For example, the amount of tinting may be measured in levels (e.g., level 1, level 2, level 3, etc.), percentages (e.g., 25%, 50%, 84%, etc.), values (e.g., parts per square inch, darkness scale, etc.), and the like. In one embodiment, a wearer may input a desired amount of tinting. For example, a wearer may prefer the glasses get darker or lighter than the default setting and may accordingly make modifications to the default values to reflect their preference.

For example, one embodiment may determine that, based upon the ambient brightness, the rule set indicates the tinting of the glasses should be level 3. However, the glasses are currently at level 2 tinting. An embodiment may adjust the amount of tinting to level 3 to match the amount of tinting indicated by the rule set based upon the ambient brightness. As another example, one embodiment may determine that, based upon the wearer's pupil size, the rule set indicates the tinting of the glasses should be 33%. However, the glasses are currently at 50% tinting. An embodiment may adjust the amount of tinting to 33% to match the amount of tinting indicated by the rule set based upon the wearer's pupil size. In one embodiment this amount of tinting may be modified by the wearer. One embodiment may have a method for wearer input (e.g., button, dial, connection to an information handling device, wireless connection, etc.) where the wearer can indicate the perfect level of tinting. For example, an embodiment may have a button the wearer may push when the amount of tinting is at their preferred level. This value may then be stored and used within the rule set.

Additionally or alternatively, one embodiment may have a default desired pupil size and may monitor the pupil size and adjust the tinting until that desired pupil size is reached. For example, as a wearer walks into a lighter location, an embodiment may monitor the wearer's pupil size. As the pupil size decreases an embodiment may continually increase the tinting until the pupil size stabilizes at the desired pupil size. In other words, rather than having a particular amount of tinting associated with a particular pupil size, an embodiment may just have a desired pupil size and may adjust the amount of tinting until that desired pupil size is reached.

Accordingly, as illustrated by the example embodiments and figures, an embodiment provides a method of electronically transitioning lenses. An embodiment may capture data associated with an ambient brightness, for example, gaze tracking data, data about the wearer's eye, ambient brightness level, UV light level, and the like. For example, one embodiment may identify the size of the wearer's pupil. Additionally or alternatively, an embodiment may identify the level of ambient brightness associated with a location where the wearer is currently located or where the wearer is looking After comparing the data to a rule set, which may be configured by the wearer in one embodiment, an embodiment may determine whether the amount of tinting of the glasses should be adjusted. An embodiment may then adjust the amount of tinting accordingly.

Thus, an embodiment allows a wearer of glasses to have glasses which adjust the amount of tinting quickly based upon factors including by not limited to UV or visible light. This allows the amount of tinting of the glasses to adjust based upon factors such as the ambient brightness of where the wearer is looking or the wearer's pupil size. For example, even though a wearer may be outside, the amount of tinting may adjust based upon whether the wearer is looking at the horizon or at their information handling device. Additionally, an embodiment allows the wearer to configure the amount of tinting to their preference so the amount of tinting may be less or greater depending on the preference of the wearer, giving the wearer a pair of glasses perfectly suited to their needs.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a general purpose information handling device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
   capturing, using a sensor, data with an ambient brightness;
   comparing, using a processor, the data with a rule set;
   determining, using a processor, an amount of tinting of glasses needs adjusted based upon the comparison of the data to the rule set; and
   adjusting, using a processor, the amount of tinting of glasses.

2. The method of claim 1, wherein the data comprises data associated with the wearer's eye.

3. The method of claim 2, wherein the data associated with the wearer's eye comprises at least one of: data associated with a pupil and gaze tracking data.

4. The method of claim 3, wherein the capturing comprises: identifying a location associated with the wearer's gaze based upon the gaze tracking data and determining the ambient brightness at the location associated with the wearer's gaze.

5. The method of claim 4, wherein the rule set comprises data including a level of ambient brightness and an amount of tinting based on the level of ambient brightness, and the adjusting comprises adjusting the tinting to the amount of tinting based on the level of ambient brightness.

6. The method of claim 3, wherein the capturing comprises identifying the size of the wearer's pupil.

7. The method of claim 6, wherein the rule set comprises data including a pupil size and an amount of tinting based upon the pupil size, and the adjusting the amount of tinting comprises adjusting the tinting to the amount of tinting based upon the pupil size.

8. The method of claim 1, wherein at least one of the rule set and the amount of tinting of glasses comprises data configured by the wearer.

9. The method of claim 1, wherein the rule set comprises data including an ambient brightness profile.

10. The method of claim 1, wherein the sensor comprises a sensor selected from the group consisting of: a camera that captures visual images, an image capture device that captures non-visible light, an eye tracker, and an optical sensor.

11. An information handling device, comprising:
    a sensor;
    a processor operatively coupled to the sensor;
    a memory device that stores instructions executable by the processor to:
    capture, using the sensor, data associated an ambient;
    compare the data with a rule set;
    determine an amount of tinting of glasses needs adjusted based upon the comparison of the data to the rule set; and
    adjust the amount of tinting of glasses.

12. The information handling device of claim 11, wherein the data comprises data associated with the wearer's eye.

13. The information handling device of claim 12, wherein the data associated with the wearer's eye comprises at least one of: data associated with a pupil and gaze tracking data.

14. The information handling device of claim 13, wherein to capture comprises: identifying a location associated with the wearer's gaze based upon the gaze tracking data and determining the ambient brightness at the location associated with the wearer's gaze.

15. The information handling device of claim 14, wherein the rule set comprises data including a level of ambient brightness and an amount of tinting based on the level of ambient brightness, and the adjusting comprises adjusting the tinting to the amount of tinting based on the level of ambient brightness.

16. The information handling device of claim 13, wherein to capture comprises identifying the size of the wearer's pupil.

17. The information handling device of claim 16, wherein the rule set comprises data including a pupil size and an amount of tinting based upon the pupil size, and the adjusting the amount of tinting comprises adjusting the tinting to the amount of tinting based upon the pupil size.

18. An information handling device, comprising:
a sensor;
a processor operatively coupled to the sensor;
a memory device that stores instructions executable by the processor to:
capture, using the sensor, data associated with an ambient brightness;
receive a signal indicating tinting of glasses needs adjusted based upon the captured data; and
adjust an amount of tinting of glasses.

19. The information handling device of claim 18, wherein the instructions are further executable by the processor to send the captured data to a processor for processing.

20. The information handling device of claim 18, wherein the data comprises data associated with the wearer's eye.

21. The information handling device of claim 20, wherein the data associated with the wearer's eye comprises at least one of: data associated with a pupil and gaze tracking data.

22. An information handling device, comprising:
a processor;
a memory device that stores instructions executable by the processor to:
receive data, captured by a sensor, associated with an ambient brightness;
compare the data with a rule set; and
determine an amount of tinting of glasses needs adjusted based upon the comparison of the data to the rule set.

23. The information handling device of claim 22, wherein the rule set comprises data including a level of ambient brightness and an amount of tinting based on the level of ambient brightness, and the adjusting comprises adjusting the tinting to the amount of tinting based on the level of ambient brightness.

24. The information handling device of claim 22, wherein the rule set comprises data including a pupil size and an amount of tinting based upon the pupil size, and the adjusting the amount of tinting comprises adjusting the tinting to the amount of tinting based upon the pupil size.

25. A product, comprising:
a storage device having code stored therewith, the code being executable by a processor and comprising:
code that captures, via a sensor, data associated with a wearer's eye;
code that identifies, using a processor, at least one characteristic associated with an ambient brightness based on the captured data;
code that compares, using a processor, the at least one characteristic with a rule set;
code that determines, using a processor, an amount of tinting of glasses needs adjusted based upon the comparison of the at least one characteristic to the rule set; and
code that adjusts, using a processor, the amount of tinting of glasses.

* * * * *